(12) United States Patent
Silva Guisasola et al.

(10) Patent No.: US 7,795,435 B2
(45) Date of Patent: Sep. 14, 2010

(54) PROCESS FOR OBTAINING THE POLYMORPHIC FORM I OF FINASTERIDE

(75) Inventors: Luis Octavio Silva Guisasola, Boecillo (ES); Mario Laderas Muñoz, Boecillo (ES); Jorge Martin Juarez, Boecillo (ES)

(73) Assignee: Ragactives, S.L., Boecillo (ES)

( * ) Notice: Subject to any disclaimer, the term of this patent is extended or adjusted under 35 U.S.C. 154(b) by 815 days.

(21) Appl. No.: 11/119,027

(22) Filed: Apr. 29, 2005

(65) Prior Publication Data

US 2005/0228008 A1 Oct. 13, 2005

Related U.S. Application Data

(63) Continuation of application No. PCT/ES03/00556, filed on Oct. 29, 2003.

(30) Foreign Application Priority Data

Oct. 31, 2002 (ES) ................ 200202512

(51) Int. Cl.
*C07D 221/18* (2006.01)
*A61K 31/473* (2006.01)

(52) U.S. Cl. ........................ 546/61; 514/284

(58) Field of Classification Search ............ 546/77, 546/61
See application file for complete search history.

(56) References Cited

U.S. PATENT DOCUMENTS

| 4,377,584 | A |   | 3/1983 | Rasmusson et al. |
| 4,760,071 | A |   | 7/1988 | Rasmusson et al. |
| 5,084,574 | A |   | 1/1992 | Bhattacharya et al. |
| 5,116,983 | A |   | 5/1992 | Bhattacharya et al. |
| 5,652,365 | A | * | 7/1997 | McCauley et al. ............ 546/77 |

FOREIGN PATENT DOCUMENTS

| EP | 0298652 | A2 | 1/1989 |
| EP | 0367502 | A1 | 5/1990 |
| EP | 0428366 | A2 | 5/1991 |
| EP | 0461930 | A1 | 12/1991 |
| EP | 0462662 | A2 | 12/1991 |
| EP | 0473225 | A2 | 3/1992 |
| EP | 0478065 | B1 | 4/1992 |
| EP | 0478066 | A2 | 4/1992 |
| GB | 2338234 | A | 12/1999 |
| WO | 0102422 | A2 | 1/2001 |
| WO | 0220553 | A1 | 3/2002 |

OTHER PUBLICATIONS

Cheronis "semimicro expermental organic chemistry" p. 31-42 (1958).*
Isopropylacetate data sheet, internet (2008).*
Terbytylacetate data sheet, internet (2008).*
Toluene data sheet, internet (2008).*
Bhattacharya, A. et al.: Acylimidazoles as Versatile Synthetic Intermediates for the Preparation of Sterically Congested Amides and Ketones: A Practical Synthesis of Proscar (R), Synthetic Communications, 30(17), 2683-2690, 1990, New York, US.
McCauley, J.A., et al.: Detection and characterization of Polymorphism in the Pharmaceutical Industry, American Institute of Chemical Engineers, Symposium Series 284 (Particle Design via Crystallization), vol. 87, 58-63, 1991, New York, US.
Wawrzycka, Irena, et al.: Structural characterization of polymorphs and molecular complexes of finasteride, Journal of Molecular Structure, 474, 157-166, 1999.

* cited by examiner

*Primary Examiner*—Celia Chang
(74) *Attorney, Agent, or Firm*—Panitch Schwarze Belisario & Nadel LLP

(57) ABSTRACT

The process includes the steps of (i) dissolving finasteride in a substantially anhydrous organic solvent selected among n-butyl acetate, iso-butyl acetate, sec-butyl acetate, tert-butyl acetate, $C_5$ alkyl acetate and mixtures thereof, at a temperature equal to or lower than the boiling point of said organic solvent; (ii) slowly cooling said finasteride solution to a cooling temperature determined on the basis of the chosen solvent; (iii) maintaining the resulting suspension at the cooling temperature for a period of time equal to or less than 16 hours; and (iv) recovering the resulting solid phase containing Form I of finasteride, for example by means of filtration, and removing the solvent, for example by means of drying said crystals. The process allows for obtaining the Form I of finasteride only and in a pure form.

12 Claims, No Drawings

PROCESS FOR OBTAINING THE POLYMORPHIC FORM I OF FINASTERIDE

CROSS-REFERENCE TO RELATED APPLICATIONS

This application is a continuation of International Application No. PCT/ES2003/000556, filed Oct. 29, 2003, which was published in the Spanish language on May 13, 2004, under International Publication No. WO 2004/039828 A1, the disclosure of which is incorporated herein by reference.

BACKGROUND OF THE INVENTION

The invention refers to a process for obtaining the pure polymorphic form of finasteride called Form I.

Finasteride [5α,17β)-N-(1,1-dimethylethyl)-3-oxo-4-aza-androst-1-ene-17-carboxamide] is an inhibitor of 5-α-reductase, an enzyme which reduces testosterone to dihydrotestosterone (DHT) which is the main mediator of the androgenic activity in some organs. Finasteride can prevent or reduce the symptoms of hyperandrogenic stimulation and is used as a drug substance in multiple therapeutic applications, such as in the treatment of benign prostate hyperplasia and androgenic alopecia.

Several processes for obtaining finasteride are known [see, for example, U.S. Pat. Nos. 4,377,584, 4,760,071, 5,084,574, 5,116,983 or International patent application WO 01/02422].

Finasteride can exist in several different polymorphic forms [see, for example, European patent EP 0 599 376 B1, International patent application WO 02/20553 A1 or the scientific publication *Journal of Molecular Structure*, 474, 157-166 (1999)], among which are those called Form I and Form II, which differ from each other in their crystalline structure. The different crystalline structures which a compound can have lead to a variation in its physicochemical parameters, such as stability, dissolution rate, solubility, melting point, etc. This variation in the properties of the compound is translated into a different bioavailability thereof, especially in those cases in which the drug substance is supplied in solid form.

From the pharmaceutical point of view, it is very important to have single and pure crystalline forms for the elaboration of pure pharmaceutical forms complying with the required pure pharmaceutical product specifications. The obtainment of single crystalline forms solves the lack of reproducibility and different bioavailability problems which pharmaceutical forms have when mixtures of polymorphs are used. Different polymorphic forms can be obtained by controlling crystallization conditions.

In the particular case of finasteride, the marketed polymorphic form is Form I, which constitutes the drug substance in the medicinal product called Proscar®.

U.S. Pat. No. 5,652,365 and EP 0 599 376 B1 disclose the preparation of the polymorphic forms Form I and Form II of finasteride. Particularly, EP 0 599 376 B1 claims a process for obtaining Form I of finasteride comprising the crystallization of said Form I from ethyl acetate with a water content of up to 3.5 mg/mL, or from isopropyl acetate with a water content of up to 1.6 mg/mL at room temperature.

Patent GB 2,338,234 discloses a process for preparing Form I of finasteride comprising initial formation of a substantially insoluble complex formed by finasteride and a salt of a Group I or Group II metal of the periodic table of elements, such as lithium bromide, in the presence of a hydroxylic solvent followed by dissociation of the complex by dissolution with acidified water and recovery of the crystalline Form I of finasteride.

BRIEF SUMMARY OF THE INVENTION

Therefore the object of the present invention is to provide an alternative process for obtaining finasteride in its pharmaceutically desirable form, i.e., in its polymorphic form I (Form I).

The process for obtaining Form I of finasteride provided by the present invention is based on the fact that the inventors have observed that by hot dissolving finasteride a substantially anhydrous organic solvent, selecting among n-butyl acetate, iso-butyl acetate, sec-butyl acetate, tert-butyl acetate, C5 alkyl acetate and mixtures thereof, at a temperature equal to or lower than the boiling point of said organic solvent, slowly cooling off said solution to a determined temperature according to the chosen solvent and maintaining the temperature reached for a certain period of time, crystals of said Form I of finasteride are obtained, which can easily be recovered from the crystallization mother liquor.

The process provided in this invention allows for obtaining Form I of finasteride only and in a pure form without the occurrence of quantifiable signals of Form II, and with a high yield.

The invention provides a process for obtaining the polymorphic form of finasteride called Form I, comprising the following steps:

(a) dissolving finasteride in a substantially anhydrous organic solvent, selecting among n-butyl acetate, iso-butyl acetate, sec-butyl acetate, tert-butyl acetate, $C_5$ alkyl acetate and mixtures thereof, at a temperature equal to or lower than the boiling point of said organic solvent;

(b) cooling the finasteride solution obtained in step a) to:
  (i) a cooling temperature comprised between 20° C. and 45° C., with a cooling rate comprised between 0.1° C./min and less than 2° C./min, when said organic solvent is n-butyl acetate, iso-butyl acetate, sec-butyl acetate or tert-butyl acetate; or to
  (ii) a cooling temperature comprised between 0° C. and 45° C., with a cooling rate comprised between 0.1° C./min and less than 2° C./min, when said organic solvent is $C_5$ alkyl acetate; and (c) maintaining the suspension resulting from step b) at the cooling temperature for a period of time equal to or less than 16 hours, optionally with stirring, and (d) recovering the resulting solid phase containing Form I of finasteride, and removing the solvent.

DETAILED DESCRIPTION OF THE INVENTION

According to the present invention, finasteride, which can be obtained by means of any of the known processes [see the Background of the Invention], is dissolved in an organic solvent selecting among n-butyl acetate, iso-butyl acetate, sec-butyl acetate, tert-butyl acetate, $C_5$ alkyl acetate and mixtures thereof. The term "$C_5$ alkyl", as used in this description, refers to a linear or branched alkyl group of 5 carbon atoms, for example, isoamyl.

Said organic solvent is substantially anhydrous, i.e., its water content is equal to or less than 0.08% (w/w). Preferably, said solvent is completely deficient in water or has a minimum water content, since the presence of water favors the formation of the polymorphic form of finasteride known as Form II.

The dissolution of finasteride in the chosen solvent is favored by heating finasteride in said solvent up to the boiling point of the solvent, generally, between 80° C. and 140° C. In a particular embodiment, when the chosen solvent is n-butyl acetate or iso-butyl acetate, the dissolution of finasteride in said solvent is favored by heating the mixture to a temperature comprised between 100° C. and 120° C. In another particular embodiment, when the chosen solvent is tert-butyl acetate, said dissolution is favored by heating the mixture to a temperature comprised between 90° C. and 100° C. In another particular embodiment, when the chosen solvent is isoamyl acetate, the dissolution of finasteride in said solvent is favored by heating the mixture to a temperature comprised between 125° C. and 140° C.

Depending on the solvent chosen, the hot finasteride solution is slowly cooled to:
(i) a cooling temperature comprised between 20° C. and 45° C., with a cooling ate comprised between 0.1° C./min and less than 2° C./min, preferably between 0.2° C./min and 1.3° C./min, more preferably between 0.3° C./min and 0.5° C./min, when said organic solvent is n-butyl acetate, iso-butyl acetate, sec-butyl acetate or tert-butyl acetate; or to
(ii) a cooling temperature comprised between 0° C. and 45° C., with a cooling rate comprised between 0.1° C./min and less than 2° C./min, preferably between 0.2° C./min and 1.3° C./min, when said organic solvent is $C_5$ alkyl acetate.

At said cooling temperatures, in the conditions indicated, the formation of crystals of Form I of finasteride occurs. This step of cooling the finasteride solution can optionally be carried out with stirring, for example, between 30 rpm and 800 rpm, preferably with a stirring speed comprised between 60 rpm and 300 rpm. The resulting finasteride suspension is maintained at the cooling temperature for a period of time equal to or less than 16 hours, preferably between 1 and 6 hours.

In a particular embodiment, using n-butyl acetate or iso-butyl acetate as a solvent, cooling of the hot finasteride solution, at a temperature comprised between 100° C. and 120° C., is carried out with stirring, at a cooling rate comprised between 0.2° C./minute and 1.3° C./minute, to a cooling temperature comprised between 20° C. and 45° C., and the temperature reached is maintained for a period of time comprised between 1 and 3 hours.

In another particular embodiment, using tert-butyl acetate as a solvent, cooling of the hot finasteride solution, at a temperature comprised between 90° C. and 100° C., is carried out with stirring, at a cooling rate comprised between 0.2° C./minute and 1.3° C./minute, to a cooling temperature comprised between 20° C. and 45° C., and the temperature reached is maintained for a period of time comprised between 1 and 16 hours.

In another particular embodiment, using isoamyl acetate as a solvent, cooling of the hot finasteride solution, at a temperature comprised between 120° C. and 140° C., is carried out with stirring, at a cooling rate comprised between 0.2° C./minute and 1.3° C./minute, to a cooling temperature comprised between 0° C. and 45° C., and the temperature reached is maintained for a period of time comprised between 1 and 3 hours.

The formed crystals of Form I of finasteride can be recovered from the crystallization mother liquor by means of any standard method, for example, by means of any solid-liquid separation technique. In a particular embodiment, the formed crystals of Form I of finasteride are separated from the crystallization mother liquor by filtration. The recovery of the crystals of Form I of finasteride is generally carried out at the temperature at which the finasteride solution has been cooled.

If so desired, the Form I of finasteride thus obtained can be subjected to a drying process for the purpose of removing the solvent. Said drying can be carried out using any standard equipment and method combining temperature and drying time. In a particular embodiment, Form I of finasteride obtained according to the process provided by this invention is subjected to a vacuum drying process at a temperature of 60° C.

If so desired, the process provided by this invention includes a step of concentrating the finasteride solution before proceeding to the recovery of the crystals of Form I of finasteride. The concentration of said finasteride solution can be carried out by means of any standard method. In a particular embodiment, the concentration of the finasteride solution is carried out in heat, in a vacuum, before proceeding to its cooling.

The Form I of finasteride obtained according to the process provided by the present invention can be identified and characterized by Differential Scan Calorimetry (DSC), X-ray Diffraction Analysis (XRD) and Infrared Spectroscopy (IR).

The data obtained and disclosed in Example 1.3 allows unequivocally identifying the crystalline form of finasteride obtained as pure Form I when compared with those disclosed in European patent EP 0 599 376 B1.

According to the information provided in said European patent EP 0 599 376 B1, the features of Form I of finasteride are the following:
a Differential Scan Calorimetry (DSC) curve carried out in closed capsule and at a heating rate of 20° C./min, showing a peak with a slight endotherm at about 232° C., extrapolated to a baseline of 223° C. with an associated heat of 11 J/g, and a main melting endotherm of 261° C., extrapolated to a baseline of 258° C. with an associated heat of 89 J/g;
the X-ray Powder Diffraction (XRD) shows signals with basal spacing units of 6.44, 5.69, 5.36, 4.89, 4.55, 4.31, 3.85, 3.59 and 3.14;
the Fourier Transform Infrared Spectroscopy (FT-IR) carried out on a KBr pellet, shows typical bands at 3431, 3237, 1692, 1666, 1602 and 688 $cm^{-1}$; and
solubilities in water and cyclohexane at 25° C. are 0.05±0.02 and 0.27±0.05 mg/g, respectively.

On the other hand, the features of the Form II of finasteride are the following:
a Differential Scan Calorimetry (DSC) curve carried out in closed capsule and at a heating rate of 20° C./min, showing a single melting endotherm of 261° C., extrapolated to a baseline of 258° C. with an associated heat of 89 J/g;
the X-ray Powder Diffraction (XRD) shows signals with basal spacing units of 14.09, 10.36, 7.92, 7.18, 6.40, 5.93, 5.66, 5.31, 4.68, 3.90, 3.60 and 3.25;
the Fourier Transform Infrared Spectroscopy (FT-IR) carried out on a KBr pellet, shows typical bands at 3441, 3215, 1678, 1654, 1597, 1476 and 752 $cm^{-1}$; and
solubilities in water and cyclohexane at 25° C. are 0.16±0.02 and 0.42±0.05 mg/g, respectively.

The process provided by this invention is simple, reproducible and allows obtaining the Form I of finasteride only and in a pure form. Unlike other known processes of obtaining Form I of finasteride, it allows obtaining high yields of the Form I of finasteride, only and in a pure form, which constitutes a significant advantage at an industrial level.

The following examples illustrate the invention and should not be considered as limiting thereof. In said examples, the importance of controlling the solvent, the cooling temperature and the cooling rate of the finasteride solution is clearly shown.

Examples 1-9 illustrate obtaining the pure Form I of finasteride using n-butyl acetate as a solvent and slowly cooling the finasteride solution to a temperature comprised between 25° C. and 45° C. On the contrary, Examples 10 and 11 clearly show that when the chosen solvent is n-butyl acetate and the cooling of the finasteride solution is slowly carried out to a temperature of 0° C. (Example 10), or rapidly to a temperature of 25° C. (Example 11), a mixture of crystalline forms of finasteride is obtained.

Example 12 illustrates the obtainment of pure Form I of finasteride using iso-butyl acetate as a solvent and slowly cooling the finasteride solution to a temperature of 25° C. However when a finasteride solution in iso-butyl acetate is slowly cooled to a temperature of 0° C. (Example 19), a mixture of crystalline forms of finasteride is obtained.

Example 13 illustrates the obtainment of the pure Form I of finasteride using isoamyl acetate as a solvent and slowly cooling the finasteride solution to a temperature of 0° C.

Example 14 illustrates the obtainment of the pure Form I of finasteride using tert-butyl acetate as a solvent and slowly cooling the finasteride solution to a temperature of 25° C. However, when the finasteride in tert-butyl acetate solution is slowly cooled to a temperature of 0° C. (Example 16), a mixture of crystalline forms of finasteride is obtained.

Example 15 clearly shows that the use of methyl acetate as a solvent and the slow cooling of the finasteride solution to a temperature of 25° C. does not allow obtaining Form I of finasteride.

Examples 17 and 18 clearly show that by dissolving finasteride in n-propyl acetate and slowly cooling the finasteride solution to temperatures of 0° C. or 25° C., a mixture of crystalline forms of finasteride is obtained.

EXAMPLE 1

Obtaining Form I of Finasteride 1.1 Obtaining Finasteride

Crude finasteride is prepared dissolving 20.0 g of (5α,17β)-N-(1,1-dimethylethyl)-3-oxo-4-aza-androst-2-bromo-17-carboxamide in 60 mL of dimethylsulfoxide (DMSO), and a potassium tert-butoxide in DMSO (30.3 g of tert-butoxide in 132 mL of DMSO) is added at room temperature (25° C.) with stirring until depletion of the starting material. Once the reaction is complete, it is neutralized with acetic acid and precipitated over water at 0-5° C. The obtained precipitate is filtered, the cake is washed with cold water at 0-5° C. and is dried in a hot-air oven at 50-55° C.

1.2 Obtaining Form I of Finasteride

The polymorphic Form I of finasteride was prepared by dissolving 10.0 g of finasteride in 160 mL of substantially anhydrous n-butyl acetate (0.03% percentage water content), at 115° C., until completely dissolved. The finasteride solution was left to slowly cool, with a cooling rate of about 0.45° C./min, to a temperature of 35° C., and the resulting suspension was stirred for 3 hours. The solid phase, which contained the crystals of Form I of finasteride, was collected by means of filtration and vacuum-dried at about 60° C. The obtained yield was 76% by weight.

1.3 Characterization of Form I of Finasteride

The previously obtained polymorphic Form I of finasteride was characterized by DSC, XRD, IR and thermal analysis.

The recording of the exotherm by Differential Scan Calorimetry (DSC) was carried out in closed capsule, with a cooling rate of 10° C./min, and clearly showed the existence of a slight endotherm at about 236° C., extrapolated to a baseline of 222° C. with an associated heat of about 12 J/g and a main melting endotherm at a temperature of about 253.2° C., with an associated heat of about 71 J/g.

The X-ray Powder Diffraction graph (XRD) shows typical peaks with basal spacing units of 6.39, 5.64, 5.28, 5.13, 4.81, 4.47, 4.30, 3.83, 3.57 and 3.12.

The Infrared Spectrum (IR) shows typical bands at 3426, 3240, 1687, 1666, 1599, 1504, 814 and 688 cm$^{-1}$.

It is observed by means of thermal analysis that the decomposition of the product has two different steps: the first one between 250° C. and 400° C. with total weight loss and the second one starting from 400° C., at which temperature combustion of the product occurs.

Differential thermal analysis clearly shows a weak exothermic effect of about 240° C. and a weak endothermic effect of about 325° C., a strong endothermic effect of about 385° C., and, suddenly, a strong exothermic effect corresponding to the combustion of the product.

The obtained results clearly show that the obtained crystalline form of finasteride is unequivocally pure Form I of finasteride.

EXAMPLE 2

Obtaining Form I of Finasteride

The polymorphic Form I of finasteride was prepared by dissolving 10.0 g of finasteride in 160 mL of substantially anhydrous n-butyl acetate (0.3% percentage water content), at 115° C., until completely dissolved. The finasteride solution was left to slowly cool, with a cooling rate of about 0.45° C./min, to room temperature (25° C.), and the resulting suspension was stirred for 1.5 hours at said temperature. The solid phase, which contained the crystals of Form I of finasteride, was collected by means of filtration and vacuum-dried at about 60° C. The obtained yield was 75% by weight. The product exhibited the features indicated in Example 1.3.

EXAMPLE 3

Obtaining Form I of Finasteride

The polymorphic Form I of finasteride was prepared by dissolving 10.0 g of finasteride in 160 mL of substantially anhydrous n-butyl acetate (0.03% percentage water content), at 115° C., until completely dissolved. The finasteride solution was left to slowly cool, with a cooling rate of about 0.42° C./min, to 30° C., and the resulting suspension was stirred for 1.5 hours. The solid phase, which contained the crystals of Form I of finasteride, was collected by means of filtration and vacuum-dried at about 60° C. The obtained yield was 73% by weight. The product exhibited the features indicated in Example 1.3.

EXAMPLE 4

Obtaining Form I of Finasteride

The polymorphic Form I of finasteride was prepared by dissolving 10.0 g of finasteride in 160 mL of substantially anhydrous n-butyl acetate (0.03% percentage water content), at 115° C., until completely dissolved. The finasteride solution was left to slowly cool, with a cooling rate of about 0.38° C./min, to 45° C., and the resulting suspension was stirred for 2 hours. The solid phase, which contained the crystals of Form I of finasteride, was collected by means of filtration and vacuum-dried at about 60° C. The obtained yield was 63% by weight. The product exhibited the features indicated in Example 1.3.

EXAMPLE 5

Obtaining Form I of Finasteride

The polymorphic Form I of finasteride was prepared by dissolving 10.0 g of finasteride in 180 mL of substantially anhydrous n-butyl acetate (0.03% percentage water content), at 115° C., until completely dissolved. The finasteride solution was left to slowly cool, with a cooling rate of about 0.46° C./min, to room temperature (25° C.), and the resulting suspension was stirred for 1.5 hours. The solid phase, which contained crystals of Form I of finasteride, was collected by means of filtration and vacuum-dried at about 60° C. The obtained yield was 74% by weight. The product exhibited the features indicated in Example 1.3.

EXAMPLE 6

Obtaining Form I of Finasteride

The polymorphic Form I of finasteride was prepared by dissolving 10.0 g of finasteride in 140 mL of substantially anhydrous n-butyl acetate (0.03% percentage water content), at 115° C., until completely dissolved. The finasteride solution was left to slowly cool, with a cooling rate of about 0.45° C./min, to room temperature (25° C.), and the resulting suspension was stirred for 1.5 hours. The solid phase, which contained the crystals of Form I of finasteride, was collected by means of filtration and vacuum-dried at about 60° C. The obtained yield was 81% by weight. The product exhibited the features indicated in Example 1.3.

EXAMPLE 7

Obtaining Form I of Finasteride

The polymorphic Form I of finasteride was prepared by dissolving 10.0 g of finasteride in 160 mL of substantially anhydrous n-butyl acetate (0.03% percentage water content), at 115° C., until completely dissolved. The finasteride solution was vacuum-concentrated and left to slowly cool, with a cooling rate of about 0.45° C./min, to room temperature (25° C.), and the resulting suspension was stirred for 1.5 hours. The solid phase, which contained the crystals of Form I of finasteride, was collected by means of filtration and vacuum-dried at about 60° C. The obtained yield was 79% by weight. The product exhibited the features indicated in Example 1.3.

EXAMPLE 8

Obtaining Form I of Finasteride

The polymorphic Form I of finasteride was prepared by dissolving 10.0 g of finasteride in 140 mL of substantially anhydrous n-butyl acetate (0.03% percentage water content), at 115° C., until completely dissolved. The finasteride solution was left to slowly cool, with a cooling rate of about 0.42° C./min, 35° C., and the resulting suspension was stirred for 1 hour. The solid phase, which contained the crystals of Form I of finasteride, was collected by means of filtration and vacuum-dried at about 60° C. The obtained yield was 73% by weight. The product exhibited the features indicated in Example 1.3.

EXAMPLE 9

Obtaining Form I of Finasteride

The polymorphic Form I of finasteride was prepared by dissolving 10.0 g of finasteride in 200 mL of substantially anhydrous n-butyl acetate (0.03% percentage water content), at 115° C., until completely dissolved. The finasteride solution was left to slowly cool, with a cooling rate of about 0.25° C./min, to 45° C., and the resulting suspension was stirred for 1.5 hours. The solid phase, which contained the crystals of Form I of finasteride, was collected by means of filtration and vacuum-dried at about 60° C. The obtained yield was 70% by weight. The product exhibited the features indicated in Example 1.3.

EXAMPLE 10

Obtaining a Mixture of Crystalline Forms of Finasteride 10.0 g of finasteride were dissolved in 160 mL of substantially anhydrous n-butyl acetate (0.03% percentage water content), at 115° C., until completely dissolved. The finasteride solution was left to slowly cool, with a cooling rate of about 0.57° C./min, to 0° C., and the resulting suspension was stirred for 2 hours. The solid phase, which contained the crystals of Form I of finasteride, was collected by means of filtration and vacuum-dried at about 60° C. The obtained yield was 77% by weight. The product exhibited signals of a mixture of crystalline forms in the X-ray Powder Diffraction graph (XRD).

EXAMPLE 11

Obtaining a Mixture of Crystalline Forms of Finasteride 10.0 g of finasteride were dissolved in 160 mL of substantially anhydrous n-butyl acetate (0.03% percentage water content), at 115° C., until completely dissolved. The finasteride solution was left to slowly cool, with a cooling rate of about 2° C./min, to room temperature (25° C.), and the resulting suspension was stirred for 2 hours. The solid phase was collected by means of filtration and vacuum-dried at about 60° C. The obtained yield was 77% by weight. The product exhibited signals of a mixture of crystalline forms in the X-ray Powder Diffraction graph (XRD).

EXAMPLE 12

Obtaining Form I of Finasteride

The polymorphic Form I of finasteride was prepared by dissolving 10.0 g of finasteride in 200 mL of substantially anhydrous iso-butyl acetate (0.02% percentage water content), at 115° C., until completely dissolved. The finasteride solution was left to slowly cool, with a cooling rate of about 0.45° C./min, to room temperature (25° C.), and the resulting suspension was stirred for 3 hours. The solid phase, which contained the crystals of Form I of finasteride, was collected by means of filtration and vacuum-dried at about 60° C. The obtained yield was 77% by weight. The product exhibited the features indicated in Example 1.3.

EXAMPLE 13

Obtaining Form I of Finasteride

The polymorphic Form I of finasteride was prepared by dissolving 10.0 g of finasteride in 200 mL of substantially anhydrous isoamyl acetate (less than 0.01% percentage water content), at 130° C., until completely dissolved. The finasteride solution was left to slowly cool, with a cooling rate of about 0.7° C./min, to 0° C., and the resulting suspension was stirred for 1 hour. The solid phase, which contained the crystals of Form I of finasteride, was collected by means of filtration and vacuum-dried at about 60° C. The obtained yield was 80% by weight. The product exhibited the features indicated in Example 1.3.

EXAMPLE 14

Obtaining Form I of Finasteride

The polymorphic Form I of finasteride was prepared by dissolving 10.0 g of finasteride in 570 mL of substantially anhydrous tert-butyl acetate (0.04% percentage water content), at 95° C., until completely dissolved. The finasteride solution was left to slowly cool, with a cooling rate of about 0.40° C./min, to room temperature (25° C.), and the resulting suspension was stirred for 16 hours. The solid phase, which contained the crystals of Form I of finasteride, was collected by means of filtration and vacuum-dried at about 60° C. The obtained yield was 72% by weight. The product exhibited the features indicated in Example 1.3.

EXAMPLE 15

Crystallization in Methyl Acetate 10.0 g of finasteride were dissolved in 100 mL of substantially anhydrous methyl acetate (less than 0.01% percentage water content), at 70° C., until completely dissolved. The finasteride solution was vacuum-concentrated, left to slowly cool to room temperature (25° C.), and the resulting suspension was stirred for 1.5 hours. The solid phase was collected by means of filtration and vacuum-dried at about 60° C. The obtained yield was 23% by weight. The product did not exhibit signals of a mixture of Form I of finasteride in the X-ray Powder Diffraction graph (XRD).

EXAMPLE 16

Obtaining a Mixture of Crystalline Forms of Finasteride 10.0 g of finasteride were dissolved in 570 mL of substantially anhydrous tert-butyl acetate (less than 0.04% percentage water content), at 95° C., until completely dissolved. The finasteride solution was left to slowly cool with a cooling rate of about 0.47° C./min, to 0° C., and the resulting suspension was stirred for 1 hour. The solid phase was collected by means of filtration and vacuum-dried at about 60° C. The obtained yield was 71% by weight. The product exhibited signals of a mixture of crystalline forms in the X-ray Powder Diffraction graph (XRD).

EXAMPLE 17

Obtaining a Mixture of Crystalline Forms of Finasteride 10.0 g of finasteride were dissolved in 220 mL of substantially anhydrous n-propyl acetate (0.07% percentage water content), at 95° C., until completely dissolved. The finasteride solution was left to slowly cool, with a cooling rate of about 0.37° C./min, to room temperature (25° C.), and the resulting suspension was stirred for 2 hours. The solid phase was collected by means of filtration and vacuum-dried at about 60° C. The obtained yield was 54% by weight. The product exhibited signals of a mixture of crystalline forms in the X-ray Powder Diffraction graph (XRD).

EXAMPLE 18

Obtaining a Mixture of Crystalline Forms of Finasteride 10.0 g of finasteride were dissolved in 220 mL of substantially anhydrous n-propyl acetate (0.07% percentage water content), at 95° C., until completely dissolved. The finasteride solution was left to slowly cool, with a cooling rate of about 0.5° C./min, to 0° C., and the resulting suspension was stirred for 2 hours. The solid phase was collected by means of filtration and vacuum-dried at about 60° C. The obtained yield was 65% by weight. The product exhibited signals of a mixture of crystalline forms in the X-ray Powder Diffraction graph (XRD).

EXAMPLE 19

Obtaining a Mixture of Crystalline Forms of Finasteride 10.0 g of finasteride were dissolved in 200 mL of substantially anhydrous iso-butyl acetate (0.02% percentage water content), at 110° C., until completely dissolved. The finasteride solution was left to slowly cool, with a cooling rate of about 0.55° C./min, to 0° C., and the resulting suspension was stirred for 1.5 hours. The solid phase was collected by means of filtration and vacuum-dried at about 60° C. The obtained yield was 67% by weight. The product exhibited signals of a mixture of crystalline forms in the X-ray Powder Diffraction graph (XRD).

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A process for obtaining a pure polymorphic form of finasteride Form I, comprising the following steps:
   a) dissolving finasteride in a substantially anhydrous organic solvent selected from the group consisting of n-butyl acetate, iso-butyl acetate, sec-butyl acetate, tert-butyl acetate, and $C_5$ alkyl acetate, at a temperature equal to or about the boiling point of said organic solvent to obtain a finasteride solution;
   b) cooling the finasteride solution obtained in step a):
      i. to a cooling temperature of about 25° C. to about 45° C., with a cooling rate of about 0.25° C./min to about 0.45° C./min, when said organic solvent is n-butyl acetate, iso-butyl acetate, sec-butyl acetate or tert-butyl acetate; or
      ii. to a cooling temperature of about 0° C., with a cooling rate of about 0.25° C./min to about 0.7° C./min, when said organic solvent is $C_5$ alkyl acetate;
      to obtain a suspension, and
   c. maintaining the suspension resulting from step b) at the cooling temperature for a period of time equal to or less than 16 hours, optionally with stirring, to result in a solid phase containing the pure polymorphic form of finasteride Form I; and
   d. recovering the resulting solid phase containing the pure polymorphic form of finasteride Form I and removing the solvent.

2. A process according to claim 1, wherein said organic solvent has a water content equal to or less than 0.08% (w/w).

3. A process according to claim 1, wherein finasteride is dissolved in heat at a temperature of about 80° C. to about 140° C.

4. A process according to claim 1, wherein said solvent is n-butyl acetate, iso-butyl acetate, sec-butyl acetate or tert-butyl acetate, and the cooling rate of the finasteride solution is about 0.3° C./min to about 0.45° C./min.

5. A process according to claim 1, wherein the cooling of the finasteride solution obtained in step a) is carried out with stirring.

6. A process according to claim 1, wherein the suspension obtained in step b) is maintained at the cooling temperature for a period of time of about 1 to about 6 hours.

7. A process according to claim 1, wherein finasteride is dissolved in a solvent selected from the group consisting of n-butyl acetate and iso-butyl acetate at a temperature of about 100° C. to about 120° C., said finasteride solution is left to cool with a cooling rate of about 0.25° C./min to about 0.45° C./min to a cooling temperature of about 25° C. to about 45° C., and the suspension is maintained at said cooling temperature for a period of time of about 1 to about 3 hours.

8. A process according to claim 1, wherein finasteride is dissolved in tert-butyl acetate at a temperature of about 90° C. to about 100° C., said finasteride solution is left to cool with a cooling rate of about 0.25° C./min to about 0.45° C./min to a cooling temperature of about 25° C. to about 45° C., and the suspension is maintained at said cooling temperature for a period of time of about 1 to about 16 hours.

9. A process according to claim 1, wherein finasteride is dissolved in isoamyl acetate at a temperature of about 120° C. to about 140° C., said finasteride solution is left to cool with a cooling rate of about 0.25° C./min to about 0.7° C./min to a cooling temperature of about 0° C., and the suspension is maintained at said cooling temperature for a period of time of about 1 to about 3 hours.

10. A process according to claim 1, wherein the solid phase containing the pure polymorphic form of finasteride Form I is recovered by filtration.

11. A process according to claim 1, wherein the recovered pure polymorphic form of finasteride Form I is subjected to a drying process.

12. A process according to claim 1, further comprising a step of concentrating the finasteride solution obtained in step a) prior to step b), wherein the step of concentrating is carried out in heat and in vacuum.

* * * * *